United States Patent [19]
Fleckenstein et al.

[11] 4,157,394
[45] Jun. 5, 1979

[54] CARDIO-PROTECTIVE PHARMACEUTICAL COMPOSITION

[75] Inventors: Albrecht Fleckenstein, Ulrich; Johanna Janke, Freiburg; Klaus Lossnitzer, Bad Kissingen; Karl-Dieter Voelger, Darmstadt, all of Fed. Rep. of Germany

[73] Assignee: Rohm Pharma GmbH, Darmstadt, Fed. Rep. of Germany

[21] Appl. No.: 862,033

[22] Filed: Dec. 19, 1977

[30] Foreign Application Priority Data

Dec. 23, 1976 [DE] Fed. Rep. of Germany ....... 2658500

[51] Int. Cl.² .................. A61K 31/505; A61K 31/44; A61K 31/275
[52] U.S. Cl. ................................... 424/251; 424/263; 424/304; 424/313; 424/330
[58] Field of Search ............... 424/251, 263, 304, 313, 424/330

[56] References Cited

U.S. PATENT DOCUMENTS

| 3,081,230 | 3/1963 | Weinstock et al. ............ 424/251 |
| 3,261,859 | 7/1966 | Dengel ............................. 424/304 |

OTHER PUBLICATIONS

Costanzo et al.–Chem. Abst., vol. 84, (1976), p. 84288v.
Hohenegger et al.–Chem. Abst., vol. 85, (1976), p. 104,041k.
Luederitz et al.–Chem. Abst., vol. 84, (1976), p. 115,672x.

*Primary Examiner*—Sam Rosen
*Attorney, Agent, or Firm*—Curtis, Morris & Safford

[57] ABSTRACT

A cardio-protective pharmaceutical composition is disclosed, which composition comprises an inert carrier and a pharmaceutically-effective amount of a combination of 2,4,7-triamino-6-phenyl-pteridine (triamterene) and a calcium antagonist, such as α-isopropyl-α-[(N-methyl-N-homoveratryl)-γ-aminopropyl]-3,4-dimethoxyphenyl-acetonitrile-hydrochloride (verapamil).

5 Claims, No Drawings

CARDIO-PROTECTIVE PHARMACEUTICAL COMPOSITION

The present invention relates to a pharmaceutical composition having a cardio-protective effect.

In the preceding 20 years, increasing consideration has been given in experimental cardiology to those necrosis forms which are not, ab initio, recognizable as disturbances to the blood flow through the myocardium. Such myocardial necroses can be produced by an endogenic release of catecholamine in stress situations or by the injection of high doses of catecholamines, especially of 3,4-dihydroxy-α-[(isopropylamino)methyl]-benzyl alcohol (isoproterenol, isoprenaline).

A pre-treatment of animals with certain corticosteroids, with AT 10, vitamin D, or with an alimentary potassium-deficiency can intensify these necroses significantly. The genetically-determined heart disease known in one strain of the Syrian golden hamster, which exhibits itself by spontaneously-occurring multifocal coagulation necroses and in calcification of the heart muscle cells (cardiomyopathy), is recognized as a particularly relevant form of the disease. The hereditary disease clearly resembles several degenerative heart diseases in man. For an understanding of the origin of such myocardial necroses, a decisive finding was that they are directly attributable to a critical depletion of the myocardium in energy-rich phosphate and that an overloading of the fiber interior with calcium is responsible for this deficit in energy-rich phosphate.

The mechanistic connection between the necrosis-producing effect of catecholamines and the deleterious disappearance of energy-rich phosphate in the myocardium became clear when it could be shown that adrenalin is capable of suddenly increasing the influx of $Ca^{++}$-ions through the membrane. From this viewpoint is probably to be understood the therapeutic success which can be achieved in acute (and prophylactic) therapy using calcium-antagonistic inhibitors of electro-mechanical coupling, such as α-isopropyl-α-[(N-methyl-N-homoveratryl)-γ-aminopropyl]-3,4-dimethoxyphenyl-acetonitrile hydrochloride (verapamil); α-isopropyl-α-[N-methyl-N-homoveratryl)-γ-aminopropyl]-3,4,5-trimethoxyphenyl-acetonitrile hydrochloride (D 600); 4-(2'-nitrophenyl)-2,6-dimethyl-1,4-dihydropyridine-3,5-dicarboxylic acid dimethyl ester (nifedipine); N-(3,3-diphenylpropyl)-N-(α-methylphenethyl)-amine lactate (prenylamine); N-(3,3-diphenylpropyl)-N-(α-phenethyl)-amine-hydrochloride (fendiline); and with potassium salts and magnesium salts as physiological calcium antagonists.

The overloading of the myocardium with $Ca^{++}$-ions can also be hindered with a β-receptor blockade. In this way the attack of the isoproterenol on the myocardial fibers is directly neutralized. Probably by this mechanism, or possibly also by an unspecific membrane effect, a cardio-protective effect is attained in therapy with β-blockers. From the point of view of the calcium-antagonistic effect there is a certain graduation in effect between, on the one hand, 1-isopropylamino-3-(1-napthyloxy)-1-propane-2-ol-hydrochloride (propranolol) and, on the other hand, the "purer" β-receptor blockers having a smaller antagonistic effect [e.g. 1-(indol-4-yloxy)-3-isopropyl-aminopropane-2-ol ("Visken") or 1-(o-allyloxy-phenoxy)-3-isopropylaminopropane-2-ol-hydrochloride ("Trasicor")].

Experimental research with animals on the etiology of the above-described diseases of the heart muscle and the results of different therapeutic measures have mutually supplemented and stimulated each other. For control of the myocardium, accordingly, two principal possibilities stand open:

(a) a switching off of sympathetic stimulation by a β-receptor blockade; and (b) the inhibition of electro-mechanical coupling reactions using calcium antagonists.

These notwithstanding, the problems posed by the acute and prophylactic therapy of cardiomyopathy are in no way completely convincingly solved.

The β-blockers have taken a firm place in the treatment of heart diseases. They reduce the effect of adrenergic stimulants on the heart-circulatory system and reduce the oxygen consumption of the heart muscle. However, in certain circumstances they evoke undesired hemodynamic changes and a decrease in the coronary circulation. In diabetics, therapy with propranolol and other β-blockers and concurrent treatment with insulin or oral antidiabetics brings with it the danger of hypoglycemia. In general, the β-receptor blockers are only usable with the necessary safety when it is clear that neither cardiac decompensation nor obstructive diseases of the respiratory tract are present.

The therapeutic use of calcium-antagonists, of which verapamil can serve as a typical representative, also entails certain risks, inter alia verapamil effects a decrease in the peripheral resistance and —as a result in the decrease of pressure work—a relief of the heart. An increase in the refractory time in the AV-nodes also contributes to the anti-arrhythmic effect of verapamil.

The decrease in the peripheral resistance can under certain conditions lead to a critical decrease in blood pressure in the case of hearts which are no longer capable of maintaining a sufficient blood pressure by increasing the cardiac minute volume.

When verapamil is administered intravenously, it can lead to acute cardio-vascular side effects, such as a total AV-block, asystole, and ventricular fibrillation. The standard dosage of verapamil for oral administration is relatively high (80 mg of active agent daily). There is a firm warning against the simultaneous (intravenous) administration of verapamil and β-receptor blockers.

How the recognized high therapeutic potential of verapamil and related calcium antagonists could be utilized, if possible with a decrease in the dose administered and with the greatest possible avoidance of all therapeutic risks, is a question which has heretofore remained unanswered.

A further pharmaceutical agent which counteracts the influx of calcium into the myocardium which is induced by isoproterenol is triamterene (2,4,7-triamino-6-phenyl-pteridine). This compound already plays an important role in the therapy of edema and high blood pressure diseases.

The active agent possesses outstanding natriuretic and antikaluretic properties. In the normal organism, calciuresis and a concurrent retention of magnesium are also observed upon the administration of triamterene.

Whereas the administration of verapamil provokes a certain increase in the cardiac minute volume reflecting the fall in blood pressure, triamterene decreases the cardiac minute volume. The effects on peripheral resistance are also contrary: while verapamil decreases peripheral resistance, it is increased by triamterene.

As a result of the aforementioned contrary effects, the two active agents (as for verapamil and β-blockers) appear ab initio little-suited for simultaneous administration. It has now been found, however, that pharmaceutical compositions which contain calcium-antagonistic drugs together with triamterene surprisingly possess a significantly improved therapeutic effect, particularly a cardio-protective effect.

Calcium-antagonistic active agents which are contained together with triamterene in the pharmaceutical composition according to the present invention can be in part represented by the following formula:

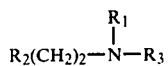  (I)

wherein $R_1$ is hydrogen or methyl,
$R_2$ is $(C_6H_5)_2CH$—(benzhydryl) or

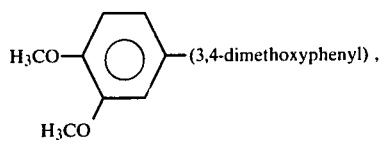

and $R_3$ is —$CH(CH_3)$—$(CH_2)_n$—$C_6H_5$
wherein n is 0 or 1, or $R_3$ is also

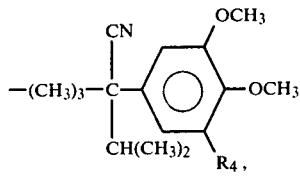

wherein $R_4$ is hydrogen or methoxy, providing that in molecules of the formula I above, either only unsubstituted phenyl groups and a secondary nitrogen atom ($R_1$=hydrogen) or methoxy-substituted phenyl and a tertiary nitrogen atom ($R_1$=methyl) are simultaneously present. Said composition may also contain pharmaceutically acceptable acid addition salts of the compounds described above, together with or instead of the compounds.

Among the pharmacologically acceptable acid addition salts can be understood, for example, the salts of d-tartaric acid, maleic acid, fumaric acid, succinic acid, citric acid, cinnamic acid, salicylic acid, adipic acid, acetic acid, propionic acid, p-amino benzoic acid, methane sulfonic acid, sulfuric acid, phosphoric acid, and particularly the hydrochloride and lactate.

Among the calcium-antagonistic active agents which can be used according to the present invention are, for example, α-isopropyl-α-[(N-methyl-N-homoveratryl)-γ-aminopropyl]-3,4,5-trimethoxyphenyl-acetonitrile-hydrochloride (D 600); 4-(2'-nitrophenyl)-2,6-dimethyl-1,4-dihydropyridine-3,5-dicarboxylic acid dimethyl ester (nifedipine); N-(3,3-diphenylpropyl)-N-(α-methyl-phenethyl)-amine lactate (prenylamine); N-(3,3-diphenylpropyl)-N-(α-phenethyl)-amine-hydrochloride (fendiline); and preferably the compound α-isopropyl-α-[(N-methyl-N-homoveratryl)-γ-aminopropyl]-3,4-dimethoxyphenyl-acetonitrile-hydrochloride (verapamil). Optionally, two or more calcium-antagonistic agents can simultaneously be part of the preparations according to the invention. By a combination of calcium-antagonistic agents, particularly verapamil and triamterene, according to the present invention, on the one hand trans-membranal calcium-permeability is reduced, for example, and, on the other hand, intracellular calcium bonding is blocked. Together, an outstanding cardio-protective effect results at smaller dosages of both active components than have been necessary in monotherapy. The effect can be demonstrated, for example, in situ in rat hearts after the induction of lesions by isoproterenol or in the earlier-mentioned cardiomyopathy of the Syrian golden hamster in the pre-necrotic stage.

The possibility, indicated by the invention, of producing a cardio-protective effect with a combination preparation which contains both active components in subnormal doses is particularly interesting for the reason that toxic nephropathy with degenerative changes has occasionally been observed in animal tests upon the continued administration of triamterene in high dosages. The preparations according to the invention are, according to present experience, free of undesired side effects and are extensively tolerable.

In the preferred embodiment, the pharmaceutical compositions according to the invention contain verapamil and triamterene in a weight ratio of 1:5 to 1:0.625, preferably in a weight ratio of 0.8:1. Dosing of the pharmaceutical preparations according to the present invention depends on the kind and severity of the disease, the age and disposition of the patient, as well as on the individual factors which are usually to be taken into consideration. In general, it will suffice to employ 75–50 percent of the normal dosages employed monotherapeutically for the calcium-antagonistic agent, preferably verapamil together with triamterene, in order to evoke the desired cardio-protective effect.

The new pharmaceutical preparations can be successfully administered parenterally and enterally. They can be prepared in the usual way and may contain the usual carriers and auxiliary agents or solvents.

Solid preparations suitable for oral administration constitute one embodiment of the invention, for example tablets, capsules, dragees, etc. For oral administration, pharmaceutically indifferent solids such as mannite, lactose, organic or inorganic calcium salts, and the like, can be used as carrier materials.

As binders, polyvinyl pyrrolidone, gelatin, or cellulose derivatives are to be considered. Further additives include tablet-rupturing agents such as starch or alginic acid, lubricants such as stearic acid or the salts thereof, and inorganic flow agents such as talc or colloidal silicic acid, as well as agents correcting the taste.

The active agents can be mixed with the auxiliaries in the usual fashion and granulated in a wet or dry condition. According to the kind of additive used, a powder which can be made directly into tablets can also be obtained by simple mixing. The granulate or powder can be filled directly into capsules or can be pressed in the usual way to form tablet cores.

Administration by ampule or suppository is also contemplated.

A better understanding of the present invention and of its many advantages will be had by referring to the following specific example given by way of illustration.

EXAMPLE 1

A pharmaceutical preparation according to the present invention having a cardio-protective effect and containing verapamil and triamterene as the active ingredients was prepared as follows:

Tablets were prepared by combining the active ingredients with inert carriers and auxiliaries in a tumble mixer in such amounts that, after pressing, the tablets had the following composition:

100.0 mg of triamterene
80.0 mg of verapamil
100.0 mg of lactose
10.0 mg of talc
5.0 mg of "Aerosil"
10.0 mg of magnesium stearate
10.0 mg of cornstarch
20.0 mg of cellulose.

What is claimed is:

1. A cardio-protective pharmaceutical composition comprising an inert carrier and a pharmaceutically-effective amount of a combination of 2,4,7-triamino-6-phenyl-pteridine and a calcium antagonist.

2. A composition as in claim 1 wherein said calcium antagonist is a compound of the formula

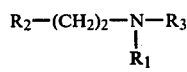

or a pharmaceutically acceptable acid addition salt thereof, wherein $R_1$ is hydrogen or methyl; $R_2$ is benzhydryl or 3,4-dimethoxyphenyl; and $R_3$ is —CH(CH$_3$)—(CH$_2$)$_n$—C$_6$H$_5$ wherein n is 0 or 1, or is

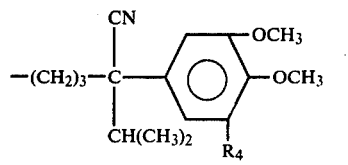

wherein $R_4$ is hydrogen or methoxy; but wherein $R_1$ is hydrogen if the compound contains unsubstituted phenyl or $R_1$ is methyl if the compound contains methoxy-substituted phenyl.

3. A composition, as in claim 1 wherein said calcium antagonist is α-isopropyl-α-[(N-methyl-N-homoveratryl)-γ-aminopropyl]-3,4-dimethoxyphenyl-acetonitrile-hydrochloride.

4. A composition as in claim 3 wherein said calcium antagonist and said 2,4,7-triamino-6-phenyl-pteridine are present in a weight ratio from 1:5 to 1:0.625.

5. A composition as in claim 4 wherein said weight ratio is 0.8:1.

* * * * *